(12) United States Patent
Tiefenbach et al.

(10) Patent No.: US 10,067,048 B2
(45) Date of Patent: Sep. 4, 2018

(54) METHOD FOR CONTROLLING THE FUNCTION OF A SENSOR FOR DETECTING PARTICLES

(71) Applicant: Robert Bosch GmbH, Stuttgart (DE)

(72) Inventors: Andy Tiefenbach, Vaihingen-Horrheim (DE); Benjamin Gaertner, Neureut (DE); Mathias Klenk, Loechgau (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/515,945

(22) PCT Filed: Aug. 13, 2015

(86) PCT No.: PCT/EP2015/068662
§ 371 (c)(1),
(2) Date: Mar. 30, 2017

(87) PCT Pub. No.: WO2016/055200
PCT Pub. Date: Apr. 14, 2016

(65) Prior Publication Data
US 2017/0299490 A1    Oct. 19, 2017

(30) Foreign Application Priority Data

Oct. 8, 2014 (DE) .................. 10 2014 220 398

(51) Int. Cl.
*G01R 27/08* (2006.01)
*G01N 15/06* (2006.01)
(Continued)

(52) U.S. Cl.
CPC ..... *G01N 15/0656* (2013.01); *G01N 15/0606* (2013.01); *G01N 27/045* (2013.01);
(Continued)

(58) Field of Classification Search
CPC .......... G01N 15/0656; G01N 15/0606; G01N 27/123; G01N 27/125; G01N 27/045; G01N 27/04; G01N 2015/0046; G01R 31/02
See application file for complete search history.

(56) References Cited

U.S. PATENT DOCUMENTS 8,035,404 B2 * 10/2011 Schnell .............. G01N 15/0656
324/71.4
2006/0016687 A1    1/2006 Wallace et al.
(Continued)

FOREIGN PATENT DOCUMENTS

DE    102007047081 A1    4/2009
DE    102010030634 A1    12/2011
(Continued)

OTHER PUBLICATIONS

International Search Report for PCT/EP2015/068662 dated Nov. 16, 2015.

*Primary Examiner* — Thang Le
(74) *Attorney, Agent, or Firm* — Norton Rose Fulbright US LLP; Gerard Messina

(57) ABSTRACT

A method is provided for controlling the function of a sensor for detecting particles, in particular soot particles, the sensor including at least two measuring electrodes and a substrate on which the measuring electrodes are situated. The method includes the following: carrying out a first current-voltage measurement for ascertaining a first measured variable; carrying out a second current-voltage measurement for ascertaining a second measured variable, one measuring electrode of the measuring electrodes being applied to another electrical potential; carrying out a third current-voltage measurement for ascertaining a third measured variable; an configured forming a correction value for cor-
(Continued)

recting the second measured variable with the aid of the first measured variable and the third measured variable.

12 Claims, 3 Drawing Sheets

(51) Int. Cl.
*G01N 27/04* (2006.01)
*G01N 27/12* (2006.01)
*G01N 15/00* (2006.01)

(52) U.S. Cl.
CPC ......... *G01N 27/123* (2013.01); *G01N 27/125* (2013.01); *G01N 2015/0046* (2013.01)

(56) References Cited

U.S. PATENT DOCUMENTS

| | | | |
|---|---|---|---|
| 2009/0051376 A1* | 2/2009 | Schnell | G01N 15/0656 324/724 |
| 2011/0030451 A1 | 2/2011 | Roesch et al. | |
| 2011/0088450 A1* | 4/2011 | Ante | F02D 41/1466 73/23.33 |
| 2012/0006094 A1 | 1/2012 | Yokoi et al. | |
| 2013/0256296 A1* | 10/2013 | Hocken | G01K 7/16 219/497 |
| 2013/0257460 A1* | 10/2013 | Roth | G01N 15/0656 324/699 |
| 2015/0177204 A1* | 6/2015 | Bessen | G01N 15/0656 73/1.06 |

FOREIGN PATENT DOCUMENTS

| | | |
|---|---|---|
| DE | 102012210525 A1 | 12/2013 |
| DE | 102013105741 A1 | 12/2013 |
| EP | 2492676 A2 | 8/2012 |
| JP | S5840698 A | 3/1983 |
| JP | H04130258 A | 5/1992 |
| WO | 03006976 A2 | 1/2003 |
| WO | 2013189806 A1 | 12/2013 |

\* cited by examiner

METHOD FOR CONTROLLING THE FUNCTION OF A SENSOR FOR DETECTING PARTICLES

FIELD OF THE INVENTION

The present invention relates to sensors for detecting particles, in particular soot particles, in an exhaust gas flow of an internal combustion engine.

BACKGROUND INFORMATION

Numerous methods and devices for detecting particles, for example, soot or dust particles, are known from the related art.

It is believed to understood from practice to measure a concentration of particles, for example soot or dust particles, in an exhaust gas with the aid of two electrodes which are situated on a ceramic. This may take place, for example, by measuring the electrical resistance of the ceramic material separating the two electrodes from one another. Sensors of this type are used, for example, in an exhaust tract of an internal combustion engine, such as a combustion engine of the diesel design. These sensors are usually located downstream from the internal combustion engine or the diesel particulate filter. As a consequence of increasing environmental awareness and, to some extent, due to statutory regulations, soot emissions must be monitored during the driving operation of a motor vehicle and the functionality of this monitoring must be ensured in the future. This type of monitoring of the functionality is, in general, referred to as on-board diagnostics. Today, particle sensors are used, for example, for monitoring the soot emissions of internal combustion engines and for on-board diagnostics (OBD), for the purpose of monitoring the function of particle filters, for example. In this context, collecting, resistive particle sensors are known which evaluate a change in the electrical properties of an interdigital electrode structure based on particle accumulation. Soot sensors of this type are known from DE 101 49 333 A1 or WO 2003/006976 A2, for example.

In the case of this type of resistive particle sensors for conductive particles, two or several metallic electrodes are formed on an electrically insulating substrate, the particles, in particular soot particles, which accumulate under the effect of an electrical measuring voltage, short-circuiting the electrodes, which mesh in a comb-like manner, and a decreasing resistance or an increasing current being measurable at a constant, applied voltage. In order to regenerate the sensor element after the accumulation of soot, the soot is burned off the sensor element in certain phases with the aid of an integrated heating element. The evaluation of the sensor signal takes place in the system by comparing the setpoint tripping time, which is ascertained from a signal behavioral model, taking into consideration the raw emission model, and the actual sensor tripping time.

In order to monitor the functionality of the electrodes and thus that of the sensor in the field, a measuring voltage is applied to the electrodes at the end of the regeneration. This results in an ionic current which is caused most of the time by contaminants in the form of sodium. If this ionic current exceeds a certain threshold value the electrodes are to be considered to be intact.

In the case of the resistive particle sensor of the related art, the self-diagnosis of the measuring electrodes is based on a current measurement at elevated temperatures. As a result of the presence of sodium ions in the insulating layer under the electrode a certain, measurable electrical conductivity is present in this case. Therefore, this diagnosis is carried out during the sensor regeneration where an active heating is carried out anyway and temperatures >750° C. are reached.

Despite the numerous advantages of the methods and devices known from the related art for detecting particles, there is still room for improvement. For example, the type of self-diagnosis described above is resistant to aging only to a limited extent. According to the related art, the negative measuring electrode is connected to ground during this phase and the positive measuring electrode is also connected to ground except for the short diagnostic phase, which is why during operation, the positive heater terminal as well as parts of the heater always have an electrical potential which is positive thereto. Since the regeneration furthermore typically takes several seconds to minutes, positively charged particles, such as in particular the sodium ions, are subjected over this longer period of time to a driving force from the inside of the sensor, where the heater is located, to the surface, where the measuring electrode is located. As a result of the high sensor temperature during this phase, the sodium ions show a great mobility and migrate upward. This mobility may be measured as current and is referred to in the following as heater input. On the surface and in the layers close to the surface, the sodium ions are furthermore subjected to a driving force toward the negative electrode during those phases in which a positive potential is applied to the positive electrode and the sensor temperature is high. Eventually, the ions start concentrating on the surface. The heater input, meaning the movement of the sodium ions from the heater toward the surface, falsifies the measurement of the self-diagnosis current, meaning the movement of the sodium ions on the surface and into the layers close to the surface, and may thus lead to a false diagnosis result. This heater input is a function of the electrical potential applied to the heater and the proportion of the conductive ions in relation to the electrons.

SUMMARY OF THE INVENTION

A method for controlling the function of a sensor for detecting particles, in particular soot particles, is therefore provided which prevents the disadvantages of known methods at least for the most part and in which the accuracy of the self-diagnosis is increased by compensating the heater input.

The method according to the present invention for controlling the function of a sensor for detecting particles, in particular soot particles, the sensor including at least two measuring electrodes and one substrate, on which the measuring electrodes are situated, includes the following steps, which may be in the indicated sequence:

carrying out a first current-voltage measurement for ascertaining a first measured variable, carrying out a second current-voltage measurement for ascertaining a second measured variable, one measuring electrode of the measuring electrodes being applied to another electrical potential, carrying out a third current-voltage measurement for ascertaining a third measured variable, and forming a correction value for correcting the second measured variable with the aid of the first measured variable and the third measured variable.

Within the scope of the present invention, the expression "one measuring electrode of the measuring electrodes is applied to another electrical potential" is used to express that the electrical potential of one of the measuring electrodes differs from the electrical potential of the other, i.e., the remaining, measuring electrodes.

The first current-voltage measurement may be carried out prior to the second current-voltage measurement and the third current-voltage measurement may be carried out following the second current-voltage measurement. The first current-voltage measurement and the third current-voltage measurement may be carried out without an electrical potential being applied to the measuring electrodes. The correction value may be ascertained based on a decay behavior of the first measured variable and the third measured variable. The correction value for correcting may be subtracted from the second measured variable. The first measured variable, the second measured variable and/or the third measured variable may be an electric current. The sensor may furthermore have a heating element. The method may be carried out when the heating element is operated. The heating element may be operated by applying a permanently or periodically clocked voltage. During operation using a clocked voltage, attention must be payed to the time offset between the rising signal edge or the falling signal edge and the signal measurement remaining the same. In other words, during operation using a clocked voltage, the time interval between switching on or turning off the heating element and the particular measurements of the signal must always remain the same. The voltage applied to the heating element is essentially derived from the electrical system voltage available in the vehicle or additionally reduced from a higher voltage level to the typical 12 V to 14 V. The electrical potential applied to the one measuring electrode while carrying out the second current-voltage measurement may essentially be 8.4 V, for example, e.g. having a deviation of no more than 0.5 V.

A computer program is furthermore provided which is configured to carry out every step of the method in the way described above.

An electronic memory medium is furthermore provided on which a computer program is stored.

An electronic control unit is furthermore provided which includes an electronic memory medium as described above.

In the sense of the present invention, particles are to be understood to mean in particular electrically conductive particles, such as soot or dust particles.

Within the scope of the present invention, measuring electrodes are to be understood to mean electrodes which are suitable for measuring a current and/or a voltage. The measuring electrodes may be in particular configured as interdigital electrodes, i.e., as meshing measuring electrodes, for example one or more meshing comb structures.

Within the scope of the present invention, an electrically insulating material is to be understood to mean any material which is suitable for preventing a current flow, such as ceramic, for example.

Within the scope of the present invention, a current-voltage measurement is to be understood to mean a measurement of an electric current and/or a voltage. The measurement takes place between the measuring electrodes. Additionally, a certain voltage may be applied to the measuring electrodes and a current flow may be measured between the measuring electrodes or an electric current may be applied to the measuring electrodes and a voltage may be measured between the measuring electrodes. A current-voltage measurement may in particular be a resistance measurement, a resistance of the structure formed by the measuring electrodes and the substrate being measurable. A voltage-controlled or a voltage-regulated measurement and/or a current-controlled and/or a current-regulated measurement may take place, for example. The current and/or the voltage may be applied in the form of a continuous signal and/or also in the form of a pulsed signal. For example, a direct voltage and/or a direct current may be applied and a current response and/or a voltage response may be detected. Alternatively, a pulsed voltage and/or a pulsed current may be applied and a current response and/or a voltage response may be detected.

Within the scope of the present invention, a measured variable is to be understood to mean a variable which is ascertained with the aid of the current-voltage measurement and which may accordingly be an electric current or a voltage. An electrical resistance derived therefrom may also be used as a measured variable.

Within the scope of the present invention, carrying out a current-voltage measurement prior to or following a certain point in time is to be understood to mean carrying out the current-voltage measurement in such a way that the current-voltage measurement is essentially carried out within a narrow time frame of that point in time, i.e., having a time offset of no more than one second.

Within the scope of the present invention, an electronic control unit is to be understood to mean any device which is suitable for carrying out the method according to the present invention, while carrying out the appropriate control and/or regulation processes. The control unit may be a separate control unit which is assigned to the sensor or also a part of a control unit of an internal combustion engine, e.g., a part of an engine controller of an internal combustion engine, in particular a diesel engine.

A basic idea of the present invention is to measure the heater input prior to and following the actual measuring pulse during the diagnostic phase and to compute from the measured values an error contribution at the point in time of the measuring pulse with the aid of a mathematical model and to subtract this error contribution from the actual measured value. This may be implemented in the control unit of the sensor or by expanding the self-diagnosis measurement. For example, the heater input initially measured prior to the measuring pulse of the diagnostic phase. Subsequently, the measured value is measured during the application of the measuring pulse of the diagnostic phase, i.e., the heater input and the self-diagnostics current. Subsequently, the heater input is measured following the measuring pulse of the diagnostic phase. Thereafter, a correction value is computed based on the decay behavior of the heater input prior to and following the measuring pulse. For example, the correction value is subtracted from the measured value during the application of the measuring pulse of the diagnostics phase.

The implementation of the method according to the present invention may take place via software. For example, the implementation may take place in the form of a computer program which may be stored on an electronic memory medium.

The cations, such as sodium ions, which by design are driven from the depth of the sensor element toward the negative measuring electrode during the self-diagnosis no longer falsify the result of the self-diagnosis as a result of the present invention. Only that current is diagnosed which is generated by the measuring pulse. Changing the heater input over the service life of the sensor has no effect on the diagnosis result.

In the case of a separated positive measuring electrode, more cations, such as sodium ions, migrate toward the negative measuring electrode and increase the heater input on the negative measuring electrode. The present invention compensates for this increased heater input and delivers the correct diagnosis result in this case: sensor defect.

Furthermore, no changes in the hardware of the sensor or the associated control unit are necessary. The change in the measuring sequence and the correction value computations are implementable with the aid of software.

Other optional details and features of the present invention result from the following description of exemplary embodiments, which are schematically shown in the figures.

DETAILED DESCRIPTION

Figure 1:
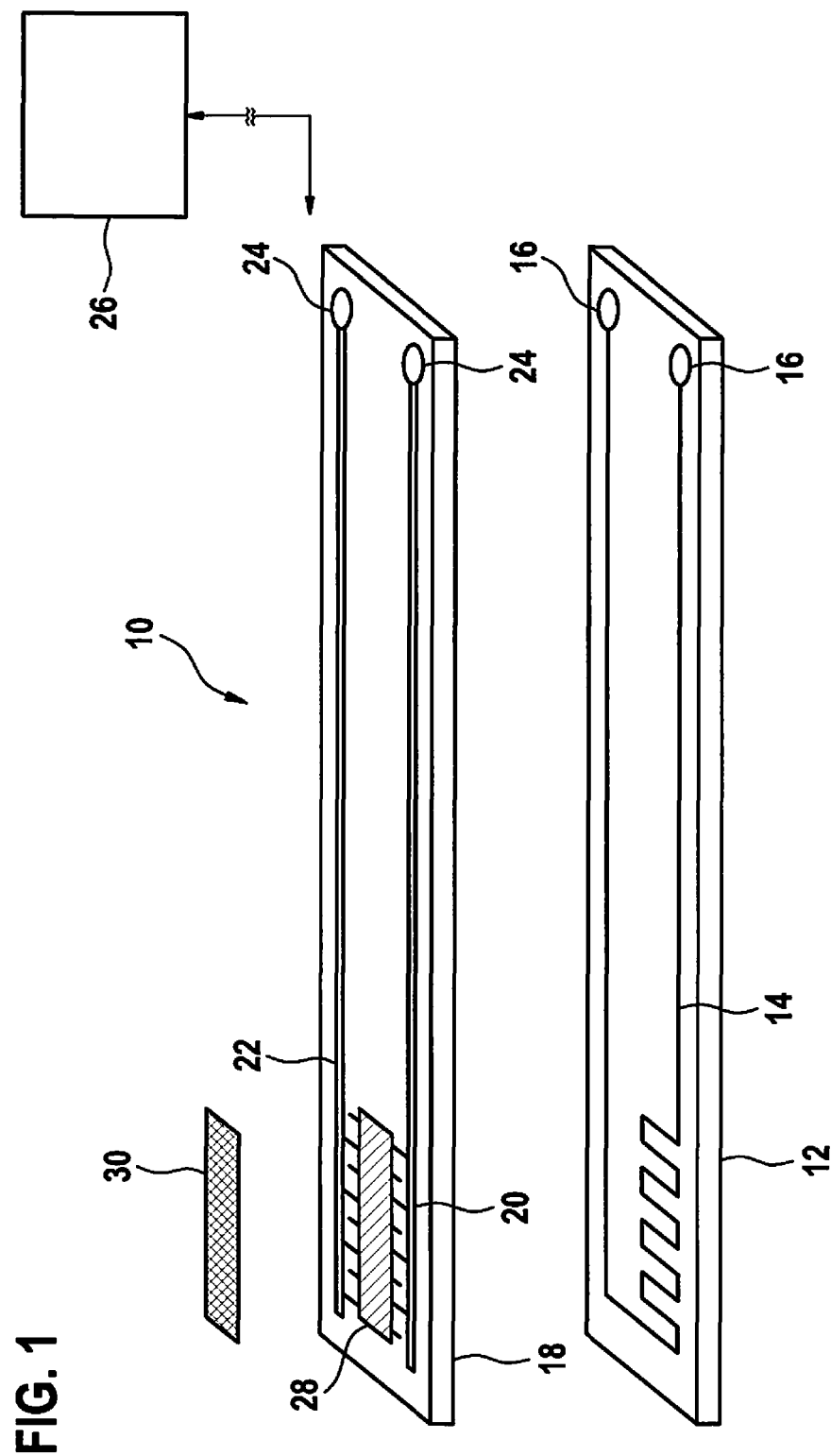
FIG. 1 shows an exploded view of a sensor for detecting particles.

FIG. 1 shows a sensor 10 for detecting particles, in particular soot particles, in a gas flow, such as in an exhaust gas flow of an internal combustion engine which is used for installation into an exhaust tract of a motor vehicle. Sensor 10 is configured as a soot sensor, for example, and may be situated downstream from a soot filter of a motor vehicle having a diesel combustion engine.

Sensor 10 includes a carrier layer 12 which may be manufactured at least partially from an electrically insulating material, e.g., a ceramic, such as aluminum oxide. Into carrier layer 12, a heating element 14 is integrated which is connectable to a suitable voltage source (not shown in greater detail) via contacts 16 and which is used to burn potentially deposited particles, such as soot particles, off sensor 10.

On carrier layer 12, a plate-shaped substrate 18 is situated which may be manufactured at least partially from an electrically insulating material, e.g., a ceramic, such as aluminum oxide. A structure formed by two measuring electrodes 20, 22 is situated on substrate 18. Measuring electrodes 20, 22 are designed, for example, as interdigital electrodes so that they mesh in a comb-like manner, as shown. Measuring electrodes 20, 22 are connectable to an electronic control unit 26 via contacts 24.

In the area in which measuring electrodes 20, 22 mesh in a comb-like manner, measuring electrodes 20, 22 may be covered at least partially by a dielectric 28, so that measuring electrodes 20, 22 may be used as electrodes of a capacitor having a measurable capacitance. Dielectric 28 may, in turn, be provided with a protective layer 30 so that it is separated from the surrounding medium whereby a degeneration of dielectric 28 is excluded.

Sensor 10 may further include a housing which surrounds the structure illustrated in FIG. 1 and is not shown in FIG. 1 for the sake of simplicity of the explanation of the structure of sensor 10. For example, the housing may be configured as a catch sleeve which is provided with an opening in an area lying above measuring electrodes 20, 22 and which is used to settle a gas flow flowing in the exhaust tract so that soot particles or other particles present in the gas flow may accumulate in the area of measuring electrodes 20, 22.

Sensor 10 according to FIG. 1 may work as follows. If soot or other electrically conductive particles accumulate on substrate 18, an electrical resistance between the two measuring electrodes 20, 22 is reduced. Measuring the impedance between the two measuring electrodes 20, 22 results in a behavior which is typical for a so-called RC member. This means that the soot or particle concentration in the particular exhaust gas may be determined based on the change over time of the resistance portion of the RC member.

In order to regenerate sensor 10 the deposited particles are burned off with the aid of heating element 14, which is integrated into carrier layer 12, after a certain period of time. If sensor 10 works properly, the resistance between measuring electrodes 20, 22 should considerably increase after this so-called bake-out and may rise toward infinity. Since the mode of operation of sensor 10 for detecting the particle concentration is known per se, e.g., from the related art of WO 2003/006976 A2 named above, the typical mode of operation of sensor 10 will not be discussed here in greater detail and the content of the related art named above which relates to the description of the functionality of sensor 10 is completely included herein by this reference. Instead, the method according to the present invention for controlling the function of sensor 10 is described in the following. The method may, for example, be carried out by control unit 26 named above. In particular, the method is described based on FIGS. 2 and 3.

Figure 2:
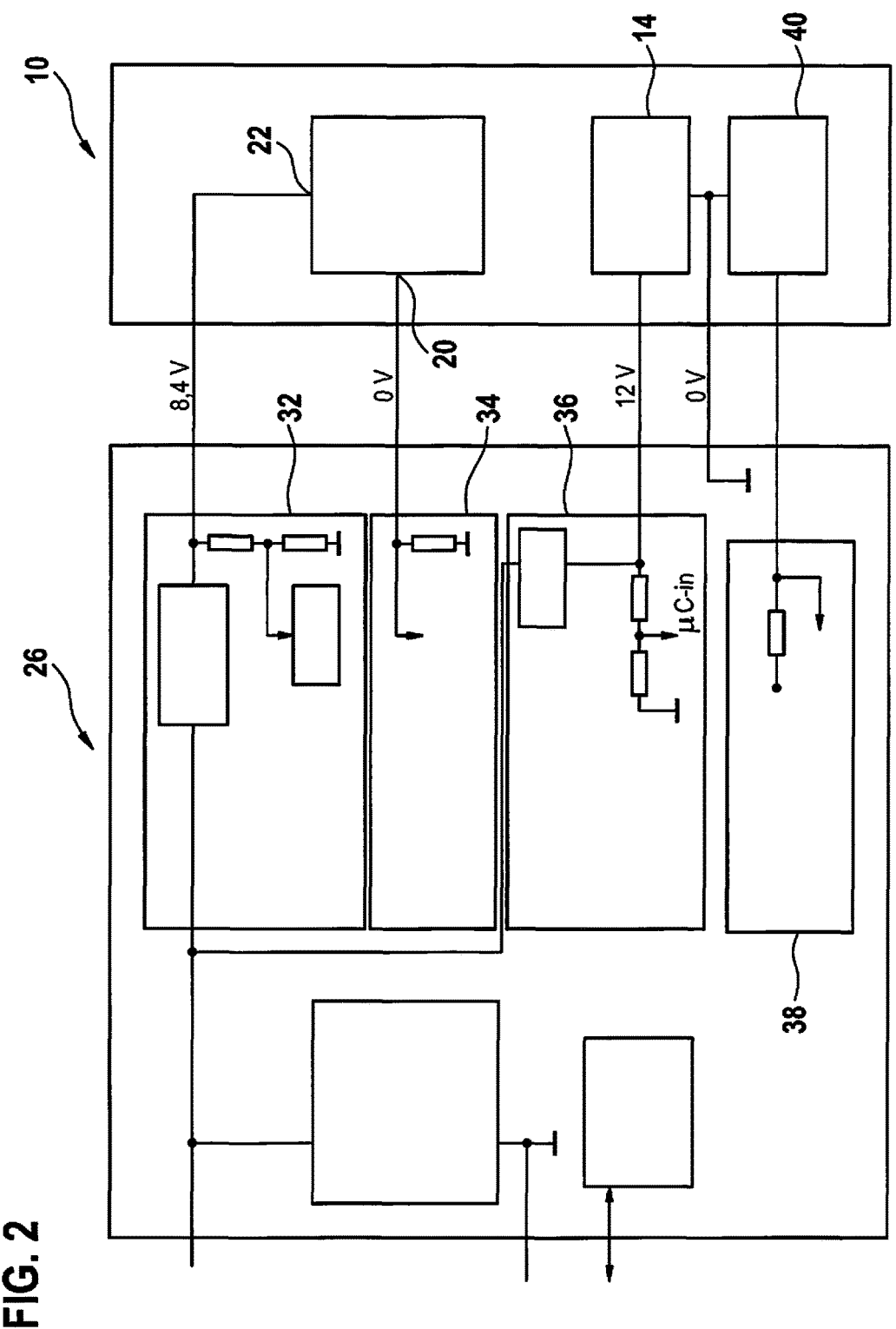
FIG. 2 shows a block diagram of the sensor including the associated control unit including possible measuring electrodes, and heating element potentials during the regeneration.

FIG. 2 shows a block diagram of sensor 10 and the activation through control unit 26 with the aid of possible electrode and heating element potentials during the regeneration. Here, control unit 26 is illustrated on the left including a circuit 32 of a voltage source and an evaluation unit 34. Furthermore, control unit 26 includes a circuit 36 for heating element 14 and an evaluation unit 38 for a temperature sensor 40 of sensor 10. Temperature sensor 40 may in this case be a part of heating element 14 so that evaluation unit 38 may determine the temperature based on a change in the electrical resistance of heating element 14. It is apparent from the illustration in FIG. 2 that heating element 14 is operated during regeneration in that a voltage of 12 V, for example, is applied to heating element 14. It is furthermore apparent from FIG. 2 that negative measuring electrode 20 is connected to ground and that an electrical potential of 8.4 V, for example, is applied to positive measuring electrode 22 during regeneration.

Figure 3:
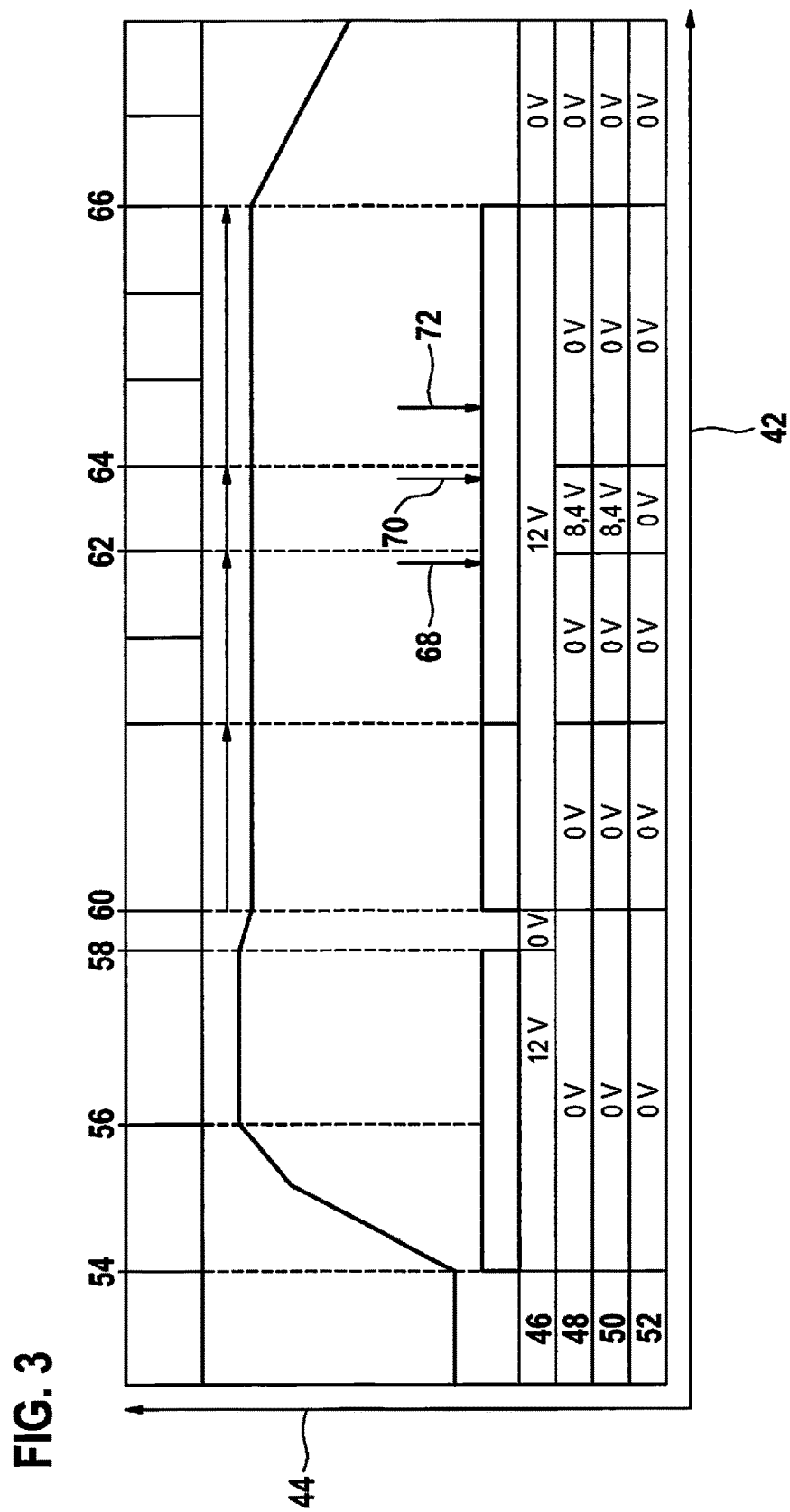
FIG. 3 shows an exemplary chronological characteristic of the electrodes and heating potentials during the regeneration phase and up to the beginning of the measuring phase.

FIG. 3 shows an exemplary chronological characteristic of electrodes and heating element potentials during the regeneration phase and up to the beginning of a measuring phase as described below in greater detail. The time is plotted on x axis 42 and the temperature is plotted on y axis 44. Located in the lines from top to bottom above x axis 42, are a voltage 46 of heating element 14 and a voltage 48 of measuring electrodes 20, 22, an electrical potential 50 of positive measuring electrode 22, and an electrical potential 52 of negative measuring electrode 20. Heating element 14 is operated at a point in time 54. Heating element 14 is operated by applying a voltage of 12 V, for example, to heating element 14. As a result, heating element 14 heats up sensor 10.

Starting from a point in time 56 particles accumulated on sensor 10, such as soot, are burned off. The burning off takes place for a time period of more than 30 seconds, for example. Toward the end of the burning off of soot, heating element 14 is temporarily not operated from a point in time 58 to a point in time 60, in that no voltage is applied to it for the purpose of reaching a defined temperature. Starting from point in time 60 heating element 14 is operated again, in that a voltage of 12 V, for example, is applied to it. No voltage is applied to measuring electrodes 20, 22 up to a point in time 62. At point in time 62, an electrical potential of 8.4 V is applied to positive measuring electrode 22. This is the actual measuring phase up to a point in time 64 as described in the following in greater detail. At point in time 64, electrical potential is no longer applied to measuring electrode 22, however heating element 14 continues to be operated up to a point in time 66. The method according to the present invention is now described in great detail in the following.

Shortly before point in time 62, a first current-voltage measurement is carried out for ascertaining a first measured variable. As illustrated in FIG. 3, for example, an electric current is measured between measuring electrodes 20, 22 shortly before point in time 62, i.e., at point in time 68, without a voltage being applied to measuring electrodes 20, 22. At a point in time 70 between points in time 62 and 64, for example shortly before point in time 64, a second current-voltage measurement is carried out for ascertaining a second measured variable. In the time period between points in time 62 and 64 and thus also at point in time 70, the electrical potential of 8.4 V is applied to positive measuring electrode 22 and the electric current between measuring electrodes 20, 22 is detected. Following point in time 64, e.g., at point in time 72, a third current-voltage measurement is carried out for ascertaining a third measured variable. At this point in time, an electrical potential is not applied to positive measuring electrode 22.

A correction value for correcting the second measured variable is formed with the aid of the first and the third measured variables. In particular, the correction value is ascertained based on a decay behavior of the first measured variable and the third measured variable. The electric current measured between measuring electrodes 20, 22 fluctuates, for example, up to point in time 68 based on the heated-up sensor element and the heater input described above.

At point in time 68, however, the first measured variable has stabilized and thus decayed to a certain value. The decay behavior of the third measured variable is ascertained analogously. Consequently, even if electrical potential is no longer applied to measuring electrode 22, a polarization takes place and thus a fluctuation of the electric current. However, the latter decays after a certain period of time so that the third measured variable may be ascertained at point in time 70. The correction value for correcting thus ascertained may then be subtracted from the second measured variable.

In other words, the operation of sensor 10 is controlled by control unit 26. In the case of an application in a motor vehicle, such as a passenger car, the electrical potentials at measuring electrodes 20, 22 and heating element 14 occur during the regeneration and up to the beginning of the actual soot collection phase, as illustrated in FIG. 2. It becomes apparent that the positive potential of heating element 14 is always, except for very short phases, higher than the two potentials of measuring electrodes 20, 22. The potential ratios during the regeneration as well as the positions of the three measuring points in time for compensating the heating input are illustrated in detail in FIG. 3. According to the method described above cations, such as sodium ions, which are by design driven from the depth of sensor 10 toward negative measuring electrode 20 during the self-diagnosis no longer falsify the result of the self-diagnosis. Only that electric current is diagnosed which is generated through the measuring pulse. Changing the heater input over the service life of the sensor no longer has an effect on the diagnosis result either.

What is claimed is:

1. A method for controlling a function of a particle sensor for detecting particles, the particle sensor including a first electrode, a second electrode, and a substrate on which the electrodes are situated, the method comprising:
   while an electrical potential applied to the first electrode is at a first level, measuring, with a current sensor, a current between the first and second electrodes, thereby obtaining a first measurement value;
   while the electrical potential applied to the first electrode is at a second level, measuring, with the current sensor, the current between the first and second electrodes, thereby obtaining a second measurement value;
   while the electrical potential applied to the first electrode is at the first level, measuring, with the current sensor, the current between the first and second electrodes, thereby obtaining a third measurement value; and
   based on the first and third measurement values, an evaluation unit determining a correction value and subtracting the correction value from the second measurement value, thereby forming a corrected particle measurement value.

2. The method of claim 1, wherein the second current measurement value is obtained subsequent to the first current measurement value being obtained and prior to the third current measurement value being obtained.

3. The method of claim 1, wherein the first and third current measurement values are obtained while the first and second electrodes are at ground potential.

4. The method of claim 1, wherein the determination of the correction value is based on a decay behavior of current ascertained based on the first and third measurement values.

5. The method of claim 1, wherein the particle sensor includes a heating element, and the measurements by which the first, second and third measurement values are obtained are performed while the heating element is operated, thereby heating the electrodes.

6. The method of claim 5, wherein the heating element is operated by applying a voltage to the heating element.

7. The method of claim 6, wherein the voltage applied to the heating element is about 12 V, and the second level of the electrical potential is about 8.4 V.

8. The method of claim 1, wherein the particles include soot particles.

9. The method of claim 1, wherein:
   the first level of the electrical potential is ground;
   the second level of the electrical potential is a positive potential;
   the measurement by which the second measurement value is obtained is performed temporally between the measurements by which the first and third measurement values are obtained; and
   the determining of the correction value includes determining a decay behavior of the current between the first and second electrodes based on the first and third measurement values, thereby identifying a contribution to the second measurement value by a behavior of current flow between the first and electrodes that is not attributable to the application of the positive potential to the first electrode, the identified contribution being the correction value.

10. A non-transitory computer readable medium on which are stored instructions that executable by a processor and that, when executed by the processor, cause the processor to perform a method for controlling a function of a particle sensor for detecting particles, the sensor including a first electrode, a second electrode, and a substrate on which the electrodes are situated, the method comprising:
- while an electrical potential applied to the first electrode is at a first level, obtaining a first measurement value of a current between the first and second electrodes;
- while the electrical potential applied to the first electrode is at a second level, obtaining a second measurement value of the current between the first and second electrodes;
- while the electrical potential applied to the first electrode is at the first level, obtaining a third measurement value of the current between the first and second electrodes; and
- based on the first and third measurement values, determining a correction value and subtracting the correction value from the second measurement value, thereby forming a corrected particle measurement value.

11. The computer readable medium of claim 10, wherein the second current measurement value is obtained subsequent to the first current measurement value being obtained and prior to the third current measurement value being obtained.

12. An electronic control unit, comprising:
a non-transitory computer readable medium on which are stored instructions that executable by a processor and that, when executed by the processor, cause the processor to perform a method for controlling a function of a particle sensor for detecting particles, the sensor including a first electrode, a second electrode, and a substrate on which the electrodes are situated, the method comprising:
- while an electrical potential applied to the first electrode is at a first level, obtaining a first measurement value of a current between the first and second electrodes;
- while the electrical potential applied to the first electrode is at a second level, obtaining a second measurement value of the current between the first and second electrodes;
- while the electrical potential applied to the first electrode is at the first level, obtaining a third measurement value of the current between the first and second electrodes; and
- based on the first and third measurement values, determining a correction value and subtracting the correction value from the second measurement value, thereby forming a corrected particle measurement value.

* * * * *